United States Patent [19]

Brittelli

[11] 4,307,232

[45] Dec. 22, 1981

[54] PREPARATION OF DIALKYL- AND DIARYLPHOSPHONOALKANOIC ACIDS AND SUBSTITUTED ACRYLIC ACIDS

[75] Inventor: David R. Brittelli, Nottingham, Pa.

[73] Assignee: E. I. Du Pont de Nemours and Company, Wilmington, Del.

[21] Appl. No.: 132,502

[22] Filed: Mar. 21, 1980

[51] Int. Cl.³ .............................................. C07C 51/00
[52] U.S. Cl. ............................. 542/454; 260/465 D; 260/941; 260/970; 562/426; 562/433; 562/434; 562/405; 562/491; 562/495; 562/598; 562/599
[58] Field of Search .................... 260/970, 941, 465 D; 562/598, 599, 491, 495, 405; 542/454

[56] References Cited

U.S. PATENT DOCUMENTS

| | | | |
|---|---|---|---|
| 2,911,435 | 11/1959 | Casioa et al. | 260/970 |
| 2,929,832 | 3/1960 | Schrader et al. | 260/970 |
| 3,897,518 | 7/1975 | Koppel | 562/495 |
| 3,974,243 | 8/1976 | Kleiner | 260/941 |

FOREIGN PATENT DOCUMENTS

| | | |
|---|---|---|
| 670529 | 9/1963 | Canada . |
| 729219 | 3/1966 | Canada . |
| 877361 | 9/1961 | United Kingdom . |

OTHER PUBLICATIONS

Coutrot et al. Synthesis 1978, (2) pp. 133–134.
Cernoyova et al. Coll Czech. Chem. Comm. 41 (1976), pp. 764–769.
Malevannaya et al. Chem. Abst. 75 (1971), #140935g.

*Primary Examiner*—Arthur P. Demers

[57] ABSTRACT

Process for preparing the substituted phosphonoalkanoic acid of the formula

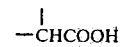
$$(R^1O)_2\overset{\overset{Y}{\|}}{P}CHR^2COOH$$

wherein:
R¹ is alkyl of 1–8 carbon atoms, aralkyl of 7–10 carbon atoms, phenyl, or substituted phenyl of 6–10 carbon atoms;
R² is H, hydrocarbyl of 1–18 carbon atoms, or substituted hydrocarbyl of 1–18 carbon atoms, wherein in said hydrocarbyl groups the carbon atom attached to the

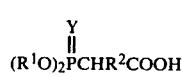
$$-\overset{|}{C}HCOOH$$

moiety is substituted with two or three hydrogen atoms or is a carbon atom of an aromatic ring; and
Y is oxygen or sulfur, which process comprises contacting and reacting, at a temperature of about −70° C. to about 125° C., a pressure of about 1–100 atmospheres (0.1–10 MPa), and for a time sufficient to effect reaction, the phosphite ester of the formula

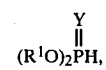
$$(R^1O)_2\overset{\overset{Y}{\|}}{P}H,$$

wherein R¹ and Y are as defined above, with the α-halocarboxylic acid of the formula R²CHXCO₂H, wherein X is Cl, Br, or I and R² is as defined above, in the presence of at least two moles of base per mole of limiting reagent, said base having a pKa greater than about 15, to produce the substituted phosphonoalkanoic acid, and process for preparing the substituted acrylic acid of the formula R³R⁴C═CR²COOH wherein:
R² is as defined above; and
R³ and R⁴ are the same or different and are selected from H, hydrocarbyl of 1–18 carbon atoms, and substituted hydrocarbyl of 1–18 carbon atoms or R³ and R⁴ taken together are cycloalkylene or substituted cycloalkylene of 4–18 carbon atoms, which process comprises:
(a) carrying out the aforesaid reaction to produce the substituted phosphonoalkanoic acid except that at least three moles of base are present; and
(b) contacting and reacting, at a temperature of about −70° to about 125° C., a pressure of about 1–100 atmospheres (0.1–10 MPa), and for a time sufficient to effect reaction, the substituted phosphonoalkanoic acid produced in step (a) with the carbonyl compound of the formula R³R⁴C═O, wherein R³ and R⁴ are as defined above, to produce the substituted acrylic acid.

9 Claims, No Drawings

PREPARATION OF DIALKYL- AND DIARYLPHOSPHONOALKANOIC ACIDS AND SUBSTITUTED ACRYLIC ACIDS

DESCRIPTION

1. Technical Field

This invention relates to the preparation of dialkyl- and diarylphosphonoalkanoic acids and to the use thereof in the preparation of substituted acrylic acids.

2. Background

Substituted acrylic acids can be prepared by such well-known classical methods as the Knoevenagel (Doebner) reaction of an aldehyde or ketone with a substituted malonic acid to obtain the acrylic acid directly. Such methods and modifications thereof may suffer from the disadvantages of long reaction times, stringent reaction conditions, unavailability of a large number of substituted malonic acids, and low yields with long chain malonic acids.

Substituted acrylic acids have also been prepared by the reaction of a dialkylphosphonoalkanoic acid with an aldehyde or ketone in the presence of a base, as disclosed, for example, in British Patent Specification No. 877,361; in U.S. Pat. No. 3,177,208; and by Coutrot et al., in Synthesis, 1978 (2), 133–134. The dialkylphosphonoalkanoic acid can be prepared by the Arbuzov reaction of a trialkyl phosphite with chloroacetic acid, for example, in 30.8% yield from triethylphosphite as disclosed by Oda et al., Kogyo Kagaku Zasshi, 70, 215–216 (1967), or it can be prepared by a multistep synthesis comprising alkylation and subsequent carboxylation, starting with diethyl phosphite, as disclosed by Coutrot et al., loc. cit.

Kosolapoff et al., "Organic Phosphorus Compounds", John Wiley & Sons, New York, 1976, 27–28, summarize the reaction of dialkyl phosphite salts with alkyl halides (Michaelis-Becker reaction). Although α-halocarboxylic acid esters react smoothly with dialkyl phosphite salts to form the corresponding dialkylphosphonoalkanoic acid esters, reaction of α-halocarboxylic acids with dialkyl phosphite salts is apparently not known. Hydrogenolysis of certain benzyl esters of dialkylphosphonoalkanoic acids to give the corresponding acids is known, as disclosed, for example, by Martin et al., J. Org. Chem., 30, 4034–4038 (1965), and Magerlein et al., J. Am. Chem. Soc., 82, 593–596 (1960), but hydrolysis or pyrolysis of certain other esters was unsuccessful, as disclosed by Magerlein et al., loc. cit.

DISCLOSURE OF INVENTION

For further comprehension of the invention, and of the objects and advantages thereof, reference may be made to the following description and to the appended claims in which the various novel features of the invention are more particularly set forth.

The invention provides a direct high-yield synthesis of dialkyl- and diarylphosphonoalkanoic acids and it also provides an improved high-yield method for the preparation of substituted acrylic acids, in one vessel if desired. More particularly, the invention resides in the process for preparing the substituted phosphonoalkanoic acid of the formula

$$(R^1O)_2PCHR^2COOH$$

wherein:

$R^1$ is alkyl of 1–8 carbon atoms, aralkyl of 7–10 carbon atoms, phenyl, or substituted phenyl of 6–10 carbon atoms;

$R^2$ is H, hydrocarbyl of 1–18 carbon atoms, or substituted hydrocarbyl of 1–18 carbon atoms, wherein said hydrocarbyl groups the carbon atom attached to the $$-\overset{|}{\underset{}{C}}HCOOH$$

moiety is substituted with two or three hydrogen atoms or is a carbon atom of an aromatic ring; and Y is oxygen or sulfur, which process comprises contacting and reacting, at a temperature of about $-70°$ C. to about $125°$ C., a pressure of about 1–100 atmospheres (0.1–10 MPa), and for a time sufficient to effect reaction, the phosphite ester of the formula

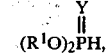

$$(R^1O)_2PH,$$

wherein $R^1$ and Y are as defined above, with the α-halocarboxylic acid of the formula $R^2CHXCO_2H$, wherein X is Cl, Br, or I and $R^2$ is as defined above, in the presence of at least two moles of base per mole of limiting reagent, said base having a pKa greater than about 15, to produce the substituted phosphonoalkanoic acid.

The invention also resides in the process for preparing the substituted acrylic acid of the formula $R^3R^4C=CR^2COOH$ wherein:

$R^2$ is as defined above; and $R^3$ and $R^4$ are the same or different and are selected from H, hydrocarbyl of 1–18 carbon atoms, and substituted hydrocarbyl of 1–18 carbon atoms or $R^3$ and $R^4$ taken together are cycloalkylene or substituted cycloalkylene of 4–18 carbon atoms, which process comprises:

(a) carrying out the aforesaid reaction to produce the substituted phosphonoalkanoic acid except that at least three moles of base are present; and (b) contacting and reacting, at a temperature of about $-70°$ to about $125°$ C., a pressure of about 1–100 atmospheres (0.1–10 MPa), and for a time sufficient to effect reaction, the substituted phosphonoalkanoic acid produced in step (a) with the carbonyl compound of the formula $R^3R^4C=O$, wherein $R^3$ and $R^4$ are as defined above, to produce the substituted acrylic acid.

The process of the invention employs readily available dialkyl- or diaryl phosphites or thionophosphites, α-halocarboxylic acids, and aldehydes or ketones. Easily preparable in high yields by means of this invention are substituted phosphonoalkanoic acids and, in a one-vessel reaction if desired, substituted acrylic acids. In a preferred embodiment of the invention, an E-cinnamic acid is prepared by reaction of a dialkyl phosphite, a haloacetic acid and an aryl aldehyde with about 3 moles of an alkali metal alkoxide. More specifically, the E-cinnamic acid is the substituted acrylic acid of the aforesaid formula wherein $R^2$ and $R^4$ are H and $R^3$ is aryl of 6–12 carbon atoms.

Since the substituted phosphonoalkanoic acid, in the form of its dianion

serves as an intermediate in the process for the preparation of the substituted acrylic acid, it is possible to separate and isolate the intermediate by neutralizing the reaction mixture before the addition of the carbonyl compound of the formula $R^3R^4C=O$. Hence, the reaction of the phosphite ester with the α-halocarboxylic acid provides a direct route to the substituted phosphonoalkanoic acid and it provides the first step of the overall process for the preparation of the substituted acrylic acid.

Dialkyl and diaryl phosphite and thionophosphite esters which are operable herein are readily available commercially or are easily prepared by well-known procedures. Examples of phosphite esters which are suitable herein include:

| | |
|---|---|
| Dimethyl phosphite | Di-n-octyl phosphite |
| Diethyl phosphite | Diphenyl phosphite |
| Di-n-propyl phosphite | Di-p-chlorophenyl phosphite |
| Diisopropyl phosphite | Di-n-tolyl phosphite |
| Di-n-butyl phosphite | Dixylyl phosphite |
| Diisobutyl phosphite | Dimethyl thionophosphite |
| Dibenzyl phosphite | Diethyl thionophosphite. |
| Di-n-hexyl phosphite | |

Preferred phosphite esters are those of the aforesaid formula wherein Y is oxygen, $R^1$ is alkyl of 1–4 carbon atoms, phenyl, or substituted phenyl of 6–10 carbon atoms wherein the substituents are selected from alkyl of 1–4 carbon atoms, Cl, Br, and I. More preferred are phosphite esters wherein Y is oxygen and $R^1$ is alkyl of 1–4 carbon atoms. Diethyl phosphite is particularly preferred because of its low cost and high solubility in a variety of solvents. α-Halocarboxylic acids are well-known in the art, and some are readily available commercially. The α-chloro and α-bromo acids can be prepared by direct halogenation of the corresponding acid, usually in the presence of a carrier, such as iodine or phosphorus trichloride. Substitution reactions can also be employed to prepare the halocarboxylic acid. For example, α-chlorophenylacetic acid can be prepared from mandelic acid and hydrochloric acid. It sometimes may be advantageous to prepare the α-haloacid by hydrolysis of the corresponding α-haloester, nitrile or acid chloride. α-Iodoacids are usually prepared by methathesis from the corresponding α-bromo compounds.

Examples of α-halocarboxylic acids which are suitable herein include:
α-Chloroacetic acid
α-Bromoacetic acid
α-Iodoacetic acid
α-Chloropropionic acid
α-Bromopropionic acid
α-Iodopropionic acid
α-Chloro-n-butyric acid
α-Bromo-n-butyric acid
α-Iodo-n-butyric acid
α-Bromo-p-fluorophenylacetic acid
α-Bromo-p-iodophenylacetic acid
α-Bromo-p-ethoxyphenylacetic acid
α-Bromo-p-trifluoromethylphenylacetic acid
α-Bromo-p-cyanophenylacetic acid
α-Bromo-m-nitrophenylacetic acid
α-Bromo-p-methylthiophenylacetic acid
α-Bromopiperonylacetic acid
α-Bromo-p-(dimethylamino)phenylacetic acid
α-Bromo-p-phenoxyphenylacetic acid
α-Bromo-p-thioacetylphenylacetic acid
α-Chloro-p-bromophenylacetic acid
α-Chlorophenylacetic acid
α-Bromophenylacetic acid
α-Bromo-n-hexanoic acid
α-Bromo-n-pentanoic acid
α-Bromo-γ-methylpentanoic acid
α-Chloro-γ-methylpentanoic acid
α-Bromo-n-decanoic acid
α-Chloro-n-decanoic acid
αBromo-n-hexadecanoic acid
α-Bromo-n-eicosanoic acid
α-Chloro-β-phenylpropionic acid
α-Bromo-β-phenylpropionic acid
α-Bromo-α-naphthylacetic acid
α-Bromo-p-chlorophenylacetic acid
α-Bromo-p-tolylacetic acid
α-Bromo-2,4-dimethylphenylacetic acid
α-Bromo-β-cyclohexylpropionic acid
α-Bromo-4-pentenoic acid.

Preferred α-halocarboxylic acids are those of the aforesaid formula wherein $R^2$ is H, alkyl of 1–14 carbon atoms, phenyl, phenylalkyl of 7–10 carbon atoms, or substituted phenyl of 6–18 carbon atoms wherein the substituents are selected from F, Cl, Br, I, alkyl of 1–8 carbon atoms, alkoxy of 1–8 carbon atoms, $CF_3$, CN, $NO_2$, thioalkyl of 1–8 carbon atoms, dialkylamino of 2–8 carbon atoms, aryloxy of 6–12 carbon atoms, thioacyl of 1–8 carbon atoms, and methylenedioxy. Particularly preferred are those of the aforesaid formula wherein $R^2$ is H, alkyl of 1–4 carbon atoms, or phenyl.

The molar amounts of phosphite ester and α-halocarboxylic acid employed in the process are not critical and an excess of either reactant can be employed. However, it is preferred, for economy, to use about equimolar amounts of phosphite ester and α-halocarboxylic acid.

The base employed in the process of the invention must be sufficiently strong to form the anion of the phosphite ester, that is, it must have a pKa greater than about 15. It is believed that the anion is formed initially in the reaction. Suitable bases include sodium hydride, potassium hydride, lithium hydride, triphenylmethyl lithium, triphenylmethyl sodium, triphenylmethyl potassium, and alkyl lithium salts. Sodium hydride is a preferred base, especially the readily available sodium hydride which is stabilized as a 50 wt % suspension in mineral oil. An alkali metal alkoxide, in combination with an alcohol solvent, is suitable and is preferred when an aromatic aldehyde or ketone is employed as a reactant.

The amount of base employed, for economic reasons, is usually the least amount required for the process. When the process of the invention is employed to prepare the substituted phosphonoalkanoic acid, at least 2 moles of base are required per mole of limiting reagent of phosphite ester or α-halocarboxylic acid. When the process of the invention is employed to prepare the substituted acrylic acid, at least 3 moles of base are required per mole of limiting reagent of phosphite ester, α-halocarboxylic acid or carbonyl compound. However, in either reaction, excess base, for example, up to about a ten-fold excess, can be employed, if desired.

The amount of base required for the process is based on the quantity of limiting reagent, that is the limiting amount of the molar quantities of the essential components of the reaction, for example, the phosphite ester, α-halocarboxylic acid, or carbonyl compound, with the proviso that sufficient additional base be present to neutralize any excess of α-halocarboxylic acid present. For example, in the preparation of the substituted acrylic acid, if the process is carried out with one mole each of phosphite ester, α-halocarboxylic acid, and carbonyl compound, at least 3 moles of base are required. If, instead, the same process is carried out with 1.5 moles of α-halocarboxylic acid, at least 3.5 moles of base are required.

The carbonyl compound employed in the process of the invention can be any of a large number of substituted and unsubstituted aliphatic, cycloaliphatic, and aromatic aldehydes and ketones. Aromatic carbonyl compounds useful herein include carbonyl group-containing carbocyclic aromatic compounds, heterocyclic compounds that show aromatic properties, and compounds containing both carbocyclic and heterocyclic rings. Examples of aldehydes and ketones which are suitable herein include:

Benzaldehyde
2-Bromobenzaldehyde
E-Cinnamaldehyde
3,4-Dichlorobenzaldehyde
3,4-Dimethoxybenzaldehyde
9-Anthraldehyde
Piperonal
3-Phenoxybenzaldehyde
2-Chlorobenzaldehyde
4-Tolualdehyde
2,4-Dimethylbenzaldehyde
1-, and 2-Anthraldehyde
3-, and 4-Bromobenzaldehyde
2-Bromo-4-cyanobenzaldehyde
5-Bromo-2-nitrobenzaldehyde
4-Chloro-3-fluorobenzaldehyde
Phenylacetaldehyde
2,4,6-Triethylbenzaldehyde
4-Vinylbenzaldehyde
4-Trifluoromethylbenzaldehyde
1-, and 2-Naphthaldehyde
2-, and 4-Biphenylcarboxaldehyde
3-Methoxy-2-anthraldehyde
Hydrocinnamaldehyde
Formaldehyde
4-Methoxybenzaldehyde
4-Nitrobenzaldehyde
Cyclohexanecarboxaldehyde
Cyclopentanecarboxaldehyde
Cycloheptanecarboxaldehyde
Acetaldehyde
Propionaldehyde
Isobutyraldehyde
n-Butyraldehyde
Hexanal
4-Pentenal
3-Methylbutanal(Isovaleraldehyde)
Octanal
Decanal
Tetradecanal
Nonadecanal
Acetone
2-Butanone
2-Pentanone
3-Pentanone
Cyclohexanone
1(2H)-Naphthalenone
3,4-Dihydro-1(2H)-naphthalenone(1-Tetralone)
2-Tetralone
Benzyl phenyl ketone
Benzophenone
Dibenzyl ketone
2-, and 3-Furaldehyde
2-, 3-, and 4-Pyridinecarboxaldehyde
3-, and 4-Quinolinecarboxaldehyde
2-, and 3-Thiophenecarboxaldehyde
Phenyl-2-pyridyl ketone
Phenyl-2-thienyl ketone
2-Decanone
2-Tetradecanone
2-Eicosanone
Propiophenone
Benzyl ethyl ketone
Acetophenone
4-Chloroacetophenone
4-Methoxyacetophenone
6-Undecanone
2-Fluorobenzaldehyde
2-Iodobenzaldehyde
4-Trifluoromethylbenzaldehyde
4-Cyanobenzaldehyde
4-Nitrobenzaldehyde
4-Methylthiobenzaldehyde
4-Dimethylaminobenzaldehyde
4-Phenoxybenzaldehyde
4-Thioactylbenzaldehyde.

Preferred carbonyl compounds are aldehydes; particularly preferred are aromatic aldehydes, unsubstituted, or substituted with 1-5 substituents selected from F, Cl, Br, I, alkoxy of 1-8 carbon atoms, alkyl of 1-8 carbon atoms, $CF_3$, CN, $NO_2$, thioalkyl of 1-8 carbon atoms, dialkylamino of 2-8 carbon atoms, aryloxy of 6-12 carbon atoms, thioacyl of 1-8 carbon atoms, and methylenedioxy; most preferred are aromatic aldehydes of 6-12 carbon atoms.

The amount of carbonyl compound employed is not critical but, preferably, an amount about equimolar with the amount of phosphite ester and the amount of α-halocarboxylic acid is used.

When preparing the substituted acrylic acid, the process of the invention can be carried out in a single reaction vessel without the need for separation or purification of the intermediate phosphonoalkanoic acid. When preparing either the phosphonoalkanoic acid or the acrylic acid, the process preferably is carried out in an inert solvent, preferably a non-hydroxylic solvent. Examples of solvents which are suitable herein include aliphatic hydrocarbons, for example, hexane and heptane; aromatic and heterocyclic compounds, for example, benzene, toluene, anisole, pyridine, and chlorobenzene; ethers, for example, diethyl ether, tetrahydrofuran, dioxane, and 1,2-dimethoxyethane; and such commonly used solvents as N,N-dimethylformamide and 1,2-difluoro-1,1,2,2-tetrachloroethane. Preferred solvents include ethers, especially 1,2-dimethoxyethane. As noted above, in the particular case when an aromatic aldehyde or ketone is employed as a reactant, an alcohol may be employed as a solvent in combination with an alkali metal alkoxide base. Preferred combinations include sodium methoxide/methanol and sodium ethoxide/ethanol.

Reaction temperature and reaction time are not critical. Reaction temperatures of about −70° C. to about 125° C. are conveniently employed. Preferably, the initial reaction temperature is ambient temperature, and the process is allowed to proceed at autogenous temperature of about 40°–50° C. Reaction times can vary from about 5 minutes to 24 hours or more, if necessary, to obtain completion of the reaction. In general, reaction rates increase with temperature and, therefore, longer reaction times are required at low reaction temperatures.

Reaction pressure is not critical and, preferably, can vary from subatmospheric pressures to superatmospheric pressures of about 100 atmospheres (10 MPa). Atmospheric pressure (about 0.1 MPa) generally is preferred.

The process is preferably carried out in a reaction vessel with stirring to allow complete mixing of reactants. Moreover, it is preferred to carry out the process in an inert atmosphere, for example, dry nitrogen, to prevent hydrolytic side-reactions of the reaction mixture with atmospheric moisture.

The order of addition of the reactants to the reaction vessel generally is not critical. For example, the phosphite ester can be added to the base, or the base can be added to the phosphite ester, and the α-halocarboxylic acid can then be added to the mixture. Alternatively, all three reactants can be mixed together simultaneously. However, in preparing the substituted acrylic acid, the carbonyl compound should not be added to the reaction mixture until after the phosphite ester, base, and α-halocarboxylic acid have been premixed.

The reaction product, that is, the substituted phosphonoalkanoic acid or the substituted acrylic acid, can be separated from the reaction mixture by acidifying the basic solution, for example, with hydrochloric acid, and then extracting the reaction product from the aqueous phase with an organic solvent. It is preferred, when the reaction product is the substituted acrylic acid, that the reaction mixture be acidified only to a pH of about 3–4 to retain the by-product phosphate in the aqueous phase. The reaction product can be separated from the organic solvent by evaporating off the solvent; the product can be purified, if desired, by such well-known techniques as crystallization.

The following examples are illustrative of the invention; all parts and percentages are by weight and all temperatures are degrees Celsius.

EXAMPLE 1

E-(trans)-Cinnamic Acid

To 4.0 ml (0.031 mole) of diethyl phosphite and 6.5 g (0.093 mole) of 97% sodium ethoxide in 100 ml of absolute ethanol was added dropwise a solution of 4.32 g (0.031 mole) of bromoacetic acid in 25 ml of absolute ethanol. The mixture was stirred for 15 min, then heated to 50° for 20 min, at which time the mixture became homogenous. Then 3.29 g (0.031 mole) of benzaldehyde was added and the mixture was stirred for 1.5 h. The solution was then poured into 500 ml of water, acidified to pH 3 with conc hydrochloric acid, and extracted with ethyl acetate. The extracts were dried (over MgSO$_4$) and evaporated in vacuo to yield 3.0 g (67%) of E-(trans)-cinnamic acid; $^1$H NMR (CDCl$_3$) δ 6.43 (1, d (J=16 Hz), =CHCO$_2$H), 7.2–7.6 (s, m, aromatic), 7.80 (1, d (J=16 Hz), PhCH=), and 11.90 (1, s, —CO$_2$H).

EXAMPLE 2

E-(trans)-cinnamic Acid

To 20.35 ml (0.093 mole) of a 24.7% solution of sodium methoxide in methanol and 25 ml of dry methanol was added 4.0 ml (0.031 mole) of diethyl phosphite. Then 4.32 g (0.031 mole) of bromoacetic acid was added. The temperature of the mixture rose to 50° autogenously. After stirring for 1.0 h at ambient temperature, 3.15 ml (0.031 mole) of benzaldehyde was added. The mixture was stirred 1.5 h and then processed as in Example 1 to yield, after recrystallizaton from n-butyl chloride, 2.4 g (48%) of E-(trans)-cinnamic acid; mp 132°–133.5° (literature mp reported in Merck Index, Eighth Edition, p 265: 133°); $^1$H NMR identical to the product of Example 1.

EXAMPLE 3

Cyclohexylideneacetic Acid

A mixture of 4.0 ml (0.031 mole) of diethyl phosphite and 4.46 g (0.093 mole) of 50% sodium hydride in mineral oil in 100 ml of 1,2-dimethoxyethane under nitrogen was treated with a solution of 2.93 g (0.031 mole) of chloroacetic acid in 30 ml of 1,2-dimethoxyethane, and the mixture was stirred until hydrogen gas evolution ceased. Then 3.20 ml (0.031 mole) of cyclohexanone was added and the mixture was stirred for 1 h, after which it was quenched by the addition of 5 ml of ethanol and then poured into 500 ml of water. The strongly basic solution was washed with ether to remove mineral oil (ether extract discarded), then acidified to pH 4 with conc hydrochloric acid and extracted with ether. The ether extract was dried (over MgSO$_4$) and evaporated in vacuo to yield 2.35 g (54%) of cyclohexylideneacetic acid which was recrystallized from methanol/water; mp 90°–91.5° (literature mp 90°–92°, Beesley, Thorpe, and Ingold, *J. Chem. Soc.*, 107, 1099 (1915)); Ir (CHCl$_3$) 3600–2400 (—OH), 1700 (C=O), and 1650 (C=C) cm$^{-1}$; $^1$H NMR (CDCl$_3$) δ 1.60 (6, s, CH$_2$CH$_2$CH$_2$CH$_2$CH$_2$C=), 2.17 (2, s, $\overline{\text{CH}_2\text{CH}_2\text{CH}_2\text{CH}_2\text{CH}_2\text{C}}$ =), 2.77 (2, s, $\overline{\text{CH}_2\text{CH}_2\text{CH}_2\text{CH}_2\text{CH}_2\text{C}}$ =), 5.50 (1, s, =CHCO$_2$H), and 11.40 (1, s, —CO$_2$H); Anal Calcd for C$_8$H$_{12}$O$_2$: C, 68.55; H, 8.63; Found: C, 68.45; H, 8.61.

EXAMPLE 4

Diethyl Carboxymethylphosphonate

A mixture of 4.0 ml (0.031 mole) of diethyl phosphite, 6.68 g (0.093 mole) of 94% sodium ethoxide, and 4.32 g (0.031 mole) of bromoacetic acid in 50 ml of absolute ethanol was heated under reflux for 1 h. Solvent was removed at reduced pressure, and the residual solid was triturated with ethyl acetate and 15 ml of conc hydrochloric acid with shaking and portionwise addition of water until all the solid was dissolved. The ethyl acetate layer was separated, dried (over MgSO$_4$), and evaporated to give 9.4 g of residual liquid diethyl carboxymethylphosphonate; $^1$H NMR spectrum confirmed the structure of this compound which is disclosed by Martin and Griffin, J. Org. Chem., 30, 4034-4038 (1965).

EXAMPLE 5

Diethyl α-Carboxyethylphosphonate

Using the general procedure of Example 4 except that α-bromopropionic acid was used in place of bromoacetic acid, sodium hydride in place of sodium ethoxide, and 1,2-dimethoxyethane in place of ethanol, diethyl α-carboxyethylphosphonate was prepared; Ir (neat) 3700–2400, 1700, and 1260 cm$^{-1}$; $^1$H NMR (CDCl$_3$) δ 1.35 (6, t (J=7 Hz), —OCH$_2$C$\underline{H}$$_3$); 1.48 (3, d of d (J=7 Hz, J$_{p\text{-}H}$=15 Hz), —PCHC$\underline{H}$$_3$), 3.06 (1, d of q (J=7 Hz, J$_{p\text{-}H}$=24 Hz), PC$\underline{H}$CH$_3$), 4.19 (4, d of t (J=7, J$_{p\text{-}H}$=7 Hz), —OC$\underline{H}$$_2$CH$_3$ ), and 10.42 (1, s, —CO$_2$$\underline{H}$); Anal Calcd for C$_7$H$_{15}$PO$_5$: C, 40.01; H, 7.19; Found: C, 39.53; H, 7.34.

EXAMPLES 6–36

The products of Examples 6–36 were prepared by the general procedures described in Examples 1–4, and the details of the preparations are summarized in Table I. In each example, unless otherwise noted, the following were used: the phosphite ester was diethyl phosphite, the solvent was 1,2-dimethoxyethane, and the base was sodium hydride. The products of Examples 6–36 are of the formula

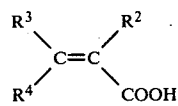

wherein R$^2$ and R$^3$ are as noted in Table I and R$^4$ is H except for Example 20 wherein it is C$_6$H$_5$ and Example 22 wherein it, together with R$^3$, is cyclopentylene. The physical properties of the products and literature references to the compounds are shown in TABLE II.

| Ex. No. | α-Haloacid | Carbonyl Compound | Crude Yield (%) | R$^2$ | R$^3$ |
|---|---|---|---|---|---|
| 6 | Choloroacetic | 2-Bromobenz-aldehyde | 51 | H | 2-BrC$_6$H$_4$ |
| 7 | α-Bromopropionic | Benzaldehyde | 82 | CH$_3$ | C$_6$H$_5$ |
| 8 | α-Bromophenyl-acetic | Benzaldehyde | 100 | C$_6$H$_5$ | C$_6$H$_5$ |
| 9 | α-Bromobutyric | Benzaldehyde | 97 | C$_2$H$_5$ | C$_6$H$_5$ |
| 10 | α-Bromophenyl-acetic | E-cinnam-aldehyde | 91 | C$_6$H$_5$ | styryl |
| 11 | Chloroacetic | Benzaldehyde | 37 | H | C$_6$H$_5$ |
| 12 | α-Bromo-n-hexadecanoic | Benzaldehyde | 85 | n-C$_{14}$H$_{29}$ | C$_6$H$_5$ |
| 13 | α-Bromophenyl-acetic | Benzaldehyde | 30 | C$_6$H$_5$ | C$_6$H$_5$ |
| 14 | α-Chloropropionic | Benzaldehyde | 100 | CH$_3$ | C$_6$H$_5$ |
| 15 | α-Bromobutyric | Benzaldehyde | 80 | C$_2$H$_5$ | C$_6$H$_5$ |
| 16 | α-Bromopropionic | E-Cinnam-aldehyde | 88 | CH$_3$ | styryl |
| 17 | α-Bromopropionic | 3,4-Dichloro-benzaldehyde | 94 | CH$_3$ | 3,4-Cl$_2$C$_6$H$_3$ |
| 18 | α-Bromophenyl-acetic | Benzaldehyde | 76 | C$_6$H$_5$ | C$_6$H$_5$ |
| 19 | α-Bromobutyric | 3,4-Dimethoxy-benzaldehyde | 85 | C$_2$H$_5$ | 3,4-(CH$_3$O)$_2$—C$_6$H$_3$ |
| 20 | Chloroacetic | Benzophenone | 30 | H | C$_6$H$_5$ |
| 21 | Chloroacetic | n-Decanal | 56 | H | n-C$_9$H$_{19}$ |
| 22 | α-Bromopropionic | Cyclohexanone | 76 | CH$_3$ | C$_5$H$_{10}$* |
| 23 | α-Bromobutyric | 9-Anthral-aldehyde | 80 | C$_2$H$_5$ | 9-C$_{14}$H$_9$ |
| 24 | Chloroacetic | n-Tetra-decanal | 28 | H | n-C$_{13}$H$_{27}$ |
| 25 | α-Bromopentanoic | Benzaldehyde | 69 | n-C$_3$H$_7$ | C$_6$H$_5$ |
| 26 | α-Bromohexanoic | Benzaldehyde | 100 | n-C$_4$H$_9$ | C$_6$H$_5$ |
| 27 | Chloroacetic | Benzaldehyde | 100 | H | C$_6$H$_5$ |
| 28 | α-Bromo-γ-methylpentanoic | Benzaldehyde | 97 | (CH$_3$)$_2$—CHCH$_2$ | C$_6$H$_5$ |
| 29 | α-Bromobutyric | Piperonal | 90 | C$_2$H$_5$ | 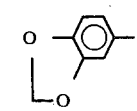 |
| 30 | α-Bromobutyric | 3-Phenoxy-benzaldehyde | 56 | C$_2$H$_5$ | 3-(C$_6$H$_5$O)C$_6$H$_4$ |
| 31–35 | α-Bromopropionic | Benzaldehyde | — | CH$_3$ | C$_6$H$_5$ |
| 36 | α-Bromopropionic | Benzaldehyde | — | CH$_3$ | C$_6$H$_5$ |

-continued

| Ex. No. | α-Haloacid | Carbonyl Compound | Crude Yield (%) | R² | R³ |
|---|---|---|---|---|---|
| | pionic | | | | |

*R³ and R⁴ together are cyclopentylene.

TABLE II

| Ex. No. | |
|---|---|
| 6. | Methanol solvent; sodium methoxide; product M.P. 217.5–218.5°; Chem. Ber., 64. p 2688 (1931). |
| 7. | M.P. 77–79°; J. Am. Chem. Soc., 80, p 4949 (1958). |
| 8. | M.P. 163–170°; Gazz. Chim. Ital., p 429 (1878). |
| 9. | M.P. 105–106.5°, J. Am. Chem. Soc., 80, p 4949 (1958). |
| 10. | IR, NMR identical to authentic sample (Aldrich Chemical Co., Milwaukee, Wisconsin). |
| 11. | Reaction temperature, 0°. |
| 12. | M.P. 83–84°; Ir (CHCl₃) 3600–2400, 1690, and 1640 cm⁻¹; ¹H NMR (CDCl₃) δ 1.27 (27, s, n-$C_{13}H_{27}$), 2.58 (2, m, =CCH₂$C_{13}H_{27}$), 7.38 (5, s, aromatic), 7.80 (1, s, —CH=), and 10.83 (1, s, —CO₂H); Anal Calcd for $C_{23}H_{36}O_2$: C, 80.18; H, 10.53; Found: C, 79.89; H, 10.37. |
| 13. | Diisopropyl phosphite was used. |
| 15. | Dimethyl phosphite was used. |
| 16. | M.P. 159–161.5°; IR (nujol mull) 3600–2500, 1670, and 1610 cm⁻¹; ¹H NMR (dmso-d₆) δ 2.03 (3, s, —CH₃), 7.05 (1, s, =CH—CH=), 7.21 (1, s, —PhCH=), 7.0–7.8 (5, m, phenyl), and 7.56 (1, s, =CH—CH=); Anal Calcd for $C_{12}H_{12}O_2$: C, 76.57; H, 6.43; Found: C, 76.71; H, 6.46. |
| 17. | M.P. 145.5–147°; Anal Calcd for $C_{10}H_8ClO_2$: C, 51.98; H, 3.49; Found: C, 51.64; H, 3.55. |
| 18. | Potassium hydride was used. |
| 19. | Anal Calcd for $C_{13}H_{16}O_4$: C, 66.09; H, 6.83; Found: C, 66.11; H, 6.85; M.P. 130–131°. |
| 20. | M.P. 158–160°; Am. Chem. J., 33, p 21 (1905). |
| 21. | Chem. Abstr., 40, p 3722 (1946). |
| 22. | M.P. 65–67°; J. Chem. Soc., p 2217 (1930). |
| 23. | M.P. 219–223°; Anal Calcd for $C_{19}H_{16}O_2$: C, 82.58; H, 5.84; Found: C, 82.43, H, 5.79. |
| 24. | M.P. 42–44°; Ann., 143, p 38 (1867). |
| 25. | M.P. 88–91°; J. Am. Chem. Soc., 54, p 334 (1932). |
| 26. | M.P. 82–84°; Rec. trav. Chim., 71, p 153 (1952). |
| 27. | Diethyl thionophosphite was used. |
| 28. | M.P. 73.5–74.5°; Anal Calcd for $C_{13}H_{16}O_2$: C, 76.44; H, 7.90; Found: C, 76.77; H, 7.84. |
| 29. | M.P. 131–132°; J. Am. Chem. Soc., 80, p 4949 (1958). |
| 30. | Anal Calcd for $C_{17}H_{16}O_3$: C, 76.10; H, 6.01; Found: C, 76.18, H, 6.19; M.P. 108–109.5°. |
| 31. | Solvent was toluene |
| 32. | Solvent was n-heptane. |
| 33. | Solvent was diethyl ether. |
| 34. | Solvent was pyridine. |
| 35. | Solvent was N,N-dimethylformamide. |
| 36. | Potassium t-butoxide was used as the base. |

Best Mode For Carrying Out the Invention

The best mode for carrying out the invention is believed to be represented by Examples 1, 2, 3, 9, 10, 12, 16, 17, 19, 25, 26, 28, 29, and 30.

Industrial Applicability

The dialkylphosphonoalkanoic acids are useful as intermediates for the preparation of the substituted acrylic acids. Substituted acrylic acids prepared by the process of the invention are a well-known class of organic chemicals which are used in the manufacture of plastics, perfumes, and medicinals.

It is to be understood that any illustration or description herein of embodiments of the invention is not intended as a limitation to such precise constructions and it is to be further understood that the right is reserved to all changes and modifications coming within the scope of the invention as defined in the appended claims.

I claim:

1. Process for preparing the substituted acrylic acid of the formula $R^3R^4C=R^2COOH$, wherein $R^3$ and $R^4$ are the same or different and are selected from H, hydrocarbyl of 1–18 carbon atoms, and substituted hydrocarbyl of 1–18 carbon atoms or $R^3$ and $R^4$ taken together are cycloalkylene or substituted cycloalkylene of 4–18 carbon atoms, and $R^2$ is H, hydrocarbyl of of 1–18 carbon atoms, or substituted hydrocarbyl of 1–18 carbon atoms, wherein said hydrocarbyl groups the carbon atom attached to the

moiety is substituted with two or three hydrogen atoms or is a carbon atom of an aromatic ring, which process comprises:

(a) contacting and reacting at a temperature of about −70° to about 125° C., a pressure of about 1–100 atmospheres (0.1–10 MPa), and for a time sufficient to effect reaction, the phosphite ester of the formula

wherein $R^1$ is alkyl of 1–8 carbon atoms, aralkyl of 7–10 carbon atoms, phenyl or substituted phenyl of 6–10 carbon atoms and Y is oxygen or sulfur, with the α-halocarboxylic acid of the formula $R^2CHXCO_2H$, wherein X is Cl, Br or I and $R^2$ is as defined above, in the presence of at least three moles of base per mole of limiting reagent, said base having a pKa greater than about 15 and being selected from sodium hydride, potassium hydride, lithium hydride, triphenylmethyl lithium, triphenylmethyl sodium, triphenylmethyl potassium and alkyl lithium salts, to produce a substituted phosphonoalkanoic acid, and (b) contacting and reacting the substituted phosphonoalkanoic acid produced, at a temperature of about −70° to about 125° C., a pressure of about 1–100 atmospheres (0.10–10 MPa), and for a time sufficient to effect reaction, with the carbonyl compound of the formula $R^3R^4C=O$, wherein $R^3$ and $R^4$ are as defined above.

2. Process of claim 1 wherein the substituted acrylic acid is recovered from the reaction mixture.

3. Process of claim 1 wherein Y is oxygen.

4. Process of claim 3 wherein $R^1$ is alkyl of 1–4 carbon atoms.

5. Process of claim 4 wherein $R^2$ is H, alkyl of 1–14 carbon atoms, phenyl, phenylalkyl of 7–10 carbon atoms, or substituted phenyl of 6–18 carbon atoms.

6. Process of claim 5 wherein $R^2$ is H, alkyl of 1–4 carbon atoms, or phenyl.

7. Process of claim 5 wherein the carbonyl compound is an aromatic aldehyde, unsubstituted, or substituted with 1-5 substituents selected from F, Cl, Br, I, alkoxy of 1-8 carbon atoms, alkyl of 1-8 carbon atoms, $CF_3$, CN, $NO_2$, thioalkyl of 1-8 carbon atoms, dialkylamino of 2-8 carbon atoms, aryloxy of 6-12 carbon atoms, thioacyl of 1-8 carbon atoms, and methylenedioxy.

8. Process of claim 7 wherein the base is sodium hydride, and an ether is employed as a solvent.

9. Process of claim 8 wherein the reaction temperature is ambient temperature $-50°$ C.